United States Patent [19]
Friedlander

[11] Patent Number: 5,313,945
[45] Date of Patent: May 24, 1994

[54] ACTIVE ATTENUATION SYSTEM FOR MEDICAL PATIENTS

[75] Inventor: Paul Friedlander, Randallstown, Md.

[73] Assignee: Noise Cancellation Technologies, Inc., Linthicum, Md.

[21] Appl. No.: 543,854

[22] PCT Filed: Sep. 18, 1989

[86] PCT No.: PCT/US89/4004
§ 371 Date: Jun. 11, 1990
§ 102(e) Date: Jun. 11, 1990

[51] Int. Cl.⁵ .......................................... A61B 5/055
[52] U.S. Cl. ................................. 128/653.2; 381/71; 381/94; 324/318
[58] Field of Search .......... 128/653 A, 653 C, 653 A, 128/653.2; 324/300, 318; 331/71, 94

[56] References Cited

U.S. PATENT DOCUMENTS

| | | | |
|---|---|---|---|
| 4,585,995 | 4/1986 | Flyan | 324/318 |
| 4,654,871 | 3/1987 | Chaplin et al. | 381/72 |
| 4,682,108 | 7/1987 | Stetler et al. | 128/653 A |
| 4,696,030 | 9/1987 | Egozi | 381/94 |
| 4,698,591 | 10/1987 | Glover et al. | 324/318 |
| 4,701,952 | 10/1987 | Taylor | 381/67 |
| 4,703,275 | 10/1987 | Holland | 324/322 |
| 4,737,716 | 4/1988 | Roener et al. | 324/319 |
| 4,903,703 | 2/1990 | Igarashi et al. | 128/653.2 |
| 4,981,137 | 1/1991 | Kondo et al. | 381/94 |
| 5,022,082 | 6/1991 | Eriksson et al. | 381/71 |
| 5,033,082 | 7/1991 | Eriksson et al. | 381/94 |
| 5,076,275 | 12/1991 | Bechor et al. | 128/653.2 |
| 5,133,017 | 7/1992 | Cain et al. | 381/71 |

FOREIGN PATENT DOCUMENTS

| | | | |
|---|---|---|---|
| 0212840 | 3/1987 | European Pat. Off. | 381/71 |
| 3627002 | 2/1988 | Fed. Rep. of Germany | 381/71 |

OTHER PUBLICATIONS

Free, John "Noise Zapper", Popular Science, Jan. 1987.

Primary Examiner—Lee S. Cohen
Assistant Examiner—Krista M. Pfaffle
Attorney, Agent, or Firm—James W. Hiney

[57] ABSTRACT

An apparatus and method of actively cancelling undesirable acoustic noise generated by a patient diagnosing apparatus during a diagnosis operation which includes a remotely located active noise cancellation unit. The undesirable acoustic noise is transferred via hollow tubes from the patient diagnosing apparatus to the remote location to be detected thereat. A control unit thereafter generates cancellation waves based upon the detected undesirable acoustic noise. The cancellation waves are transferred to the patient area via additional hollow tubes to cancel the undesirable acoustic noise. The use of hollow tubes of non-magnetic, non-metallic material ensures that the undesirable acoustic noise and the cancellation waves do not interfere with the diagnosis of operation.

24 Claims, 2 Drawing Sheets

ACTIVE ATTENUATION SYSTEM FOR MEDICAL PATIENTS

BACKGROUND OF THE INVENTION

1. Field of the Invention

The present invention is related to an active sound attenuation system for patients undergoing diagnosis in equipment which inherently produces undesirable sounds. The preferred embodiments of the invention described herein are related to such an active sound attenuation system for use with magnetic resonance imaging equipment.

2. Description of the Background Art

Magnetic resonance imaging (MRI) equipment utilizes a large magnet in which the patient lies prone while the magnet is activated to create a magnetic field. A radio signal is used to disorganize the nuclei of hydrogen molecules within the area being scanned. When the radio signal concludes, an MRI computer measures the fraction of a second that elapses before molecules re-orient themselves. Although this procedure is relatively safe and painless, the MRI magnet arrangement inherently generates disturbing undesirable noises.

Prior art arrangements have used music piped in to the patient to "mask" the generated noise. U.S. Pat. No. 4,701,952 to Taylor describes such a noise masking arrangement. Also, so-called passive noise attenuating systems such as ear plugs, noise insulation, and the like have been utilized. However, due to the very confining area that the patient must remain within for a relatively extended period of time, the inherent noises of the magnetic resonance imaging equipment can be quite disturbing, especially to patients with claustrophobic tendencies and/or patients that are ill.

SUMMARY OF THE INVENTION

An object of the present invention is to provide a sound attenuation or counternoise system that will actively cancel the noises generated during the diagnostic process. Another object of the invention is to construct a counternoise system that will not interfere with the operation of the diagnostic equipment.

The present invention achieves the above-mentioned and other objects by providing an active noise cancellation system which produces counternoise waves to cancel the disturbing, undesirable noise waves in the hearing area of the patient while the patient is in the diagnostic equipment. In especially preferred embodiments of the invention, the cancelling sound applied to the area of the patient to cancel the undesirable noise is supplied by non-magnetic lines, preferably pneumatic tubes or the like. Also, to detect the undesirable noise so as to process the same and generate the proper counternoise wave pattern, non-magnetic lines in the form of hollow tubes filled with a sound propagating medium are utilized.

In especially preferred embodiments, headsets are provided which fit over the patients ears and define a small space where the undesirable noise is detected and the counternoise is generated. Prior art arrangements such as disclosed in the above noted Taylor U.S. Pat. No. 4,701,952 utilize hollow tubes filled with sound propagating medium for piping in music or the like. According to the invention, similar tubes can also be used to communicate the counternoise wave patterns from a counternoise processing unit and counternoise wave generator or speaker disposed remote from the diagnostic equipment. Hollow tubes filled with sound propagating medium are also provided for communicating the undesirable noise to be cancelled to the processing unit. The undesirable noise detection tubes need only be spaced a small distance away from the counternoise speaker tubes so as to provide a reliable signal to the counter noise processing unit.

A microprocessor controller is provided at a remote location for processing the undesirable noise signal supplied through the noise detection tubes and for generating a corresponding counternoise signal and driving a speaker that generates counternoise waves which are then supplied as noise cancelling waves via the counternoise tubes.

In certain preferred embodiments, rather than a headset, the fittings for the noise detection tubes and the counternoise tubes are fixedly arranged in the diagnostic equipment at a position adjacent the position of the patients head and ears.

The noise cancellation system of the present invention can be used in MRI diagnostic equipment and in other environments where the region where the noise is to be cancelled can not tolerate metallic speaker wires or components due to electromagnetic interference problems and the like.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE DRAWINGS

Figure 1:
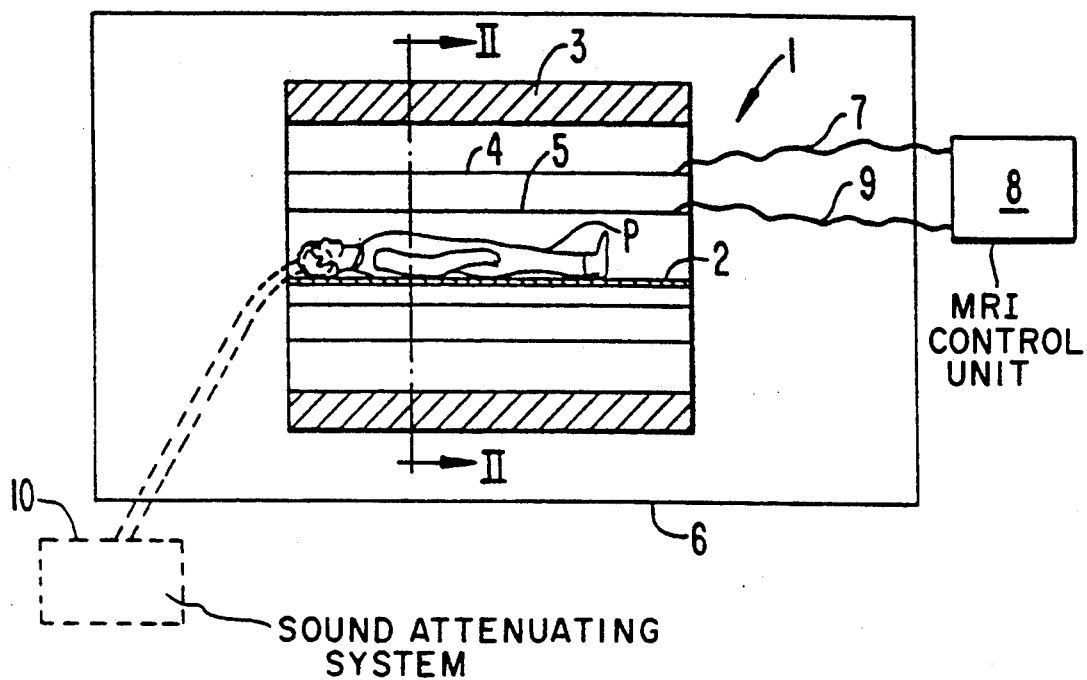
FIG. 1 is a schematic side sectional view depicting a patient in an MRI diagnostic unit with an active sound attenuation system constructed according to the present invention shown in dashed lines.
Figure 2:
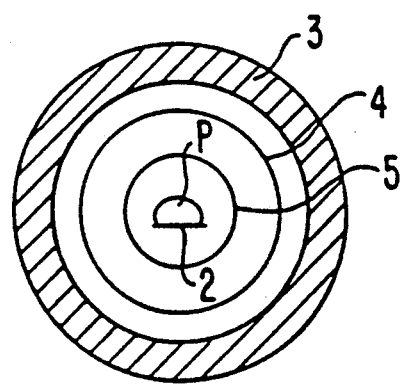
FIG. 2 is a schematic sectional view taken along the line II—II of FIG. 1.

Referring to FIGS. 1 and 2, there is schematically depicted a magnetic resonance scanning unit 1 with a human patient P in position on a table 2 for a diagnostic scanning procedure. The MRI unit 1 includes a large permanent magnet 3 which surrounds the table 2 which accommodates the patient P. Arranged concentrically within the permanent magnet 3, and also surrounding the table 2, are a magnetic coil 4 and a radio frequency RF coil 5. The entire structure with magnet 3, magnetic coil 4, RF coil 5 and patient accommodating table 2 are disposed within a shielded chamber 6 which includes shielding to prevent electromagnetic interference with the operation of the MRI control unit 8. The magnetic coil 4 is connected by circuit 7 (shown only schematically), with a MRI control unit 8. The RF coil 5 is also connected by a circuit 9 (also shown only schematically) to the MRI control unit 8.

The details of the operating circuits and parts of the MRI unit 1 are not included herein so as not to obscure the disclosure of the present invention. An MRI unit that could be used with the present invention is marketed and serviced by the company TME of Houston, Tex.

Figure 3:
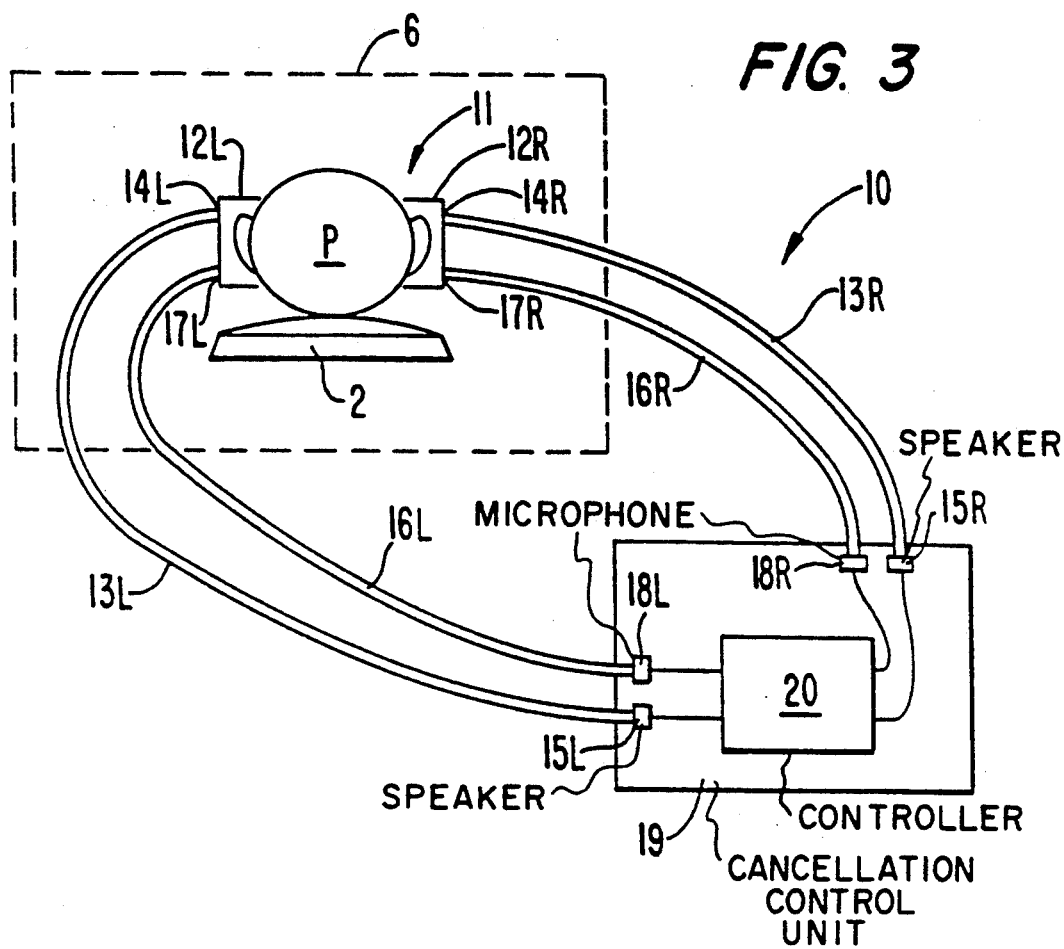
FIG. 3 is a schematic view of a headset having a closed ear coupling means arrangement and active sound attenuation system constructed according to a preferred embodiment of the present invention.

In FIG. 1, there is only a schematic depiction in dash line form of a sound attenuating system 10 for cancelling undesirable noises otherwise experienced by the patient during normal operation of the MRI unit 1. In FIG. 3, the shielded chamber walls 6 are shown only schematically in dashed outline form and further details of the sound attenuating system 10 are schematically illustrated.

Referring to FIG. 3, the sound attenuating system 10 includes a headset 11 with a right ear coupling means 12R and a left ear coupling means 12L for coupling the counternoise to the auditory system of the patient. The ear coupling means 12R, 12L comprise, for example, earpieces which have an open or closed back and which transmit the counternoise to the auditory system of the patient's body.

In a closed ear coupling means arrangement, the ear of the patient is surrounded by the ear coupling means so as to isolate the patient's ear from ambient air and to form a chamber which encloses the ear. The closed ear coupling means arrangement comprises, for example, a cup-like configuration which surrounds the ear to form a chamber as shown in FIG. 3. In an open ear coupling arrangement, the ear coupling means is placed within an effective range of the patient's ear, but is not isolated from the ambient air surrounding the patient, as best shown, for example, in FIG. 4.

A flexible hollow tube 13R extends from ear coupling means opening 14R of the ear coupling means 12R to a speaker 15R. In a similar manner, hollow tube 13L extends from opening 14L of ear coupling means 12L to an opening facing speaker 15L. A hollow tube 16R extends between an opening 17R of ear coupling means 12R to a microphone 18R. In a like manner, hollow tube 16L extends from opening 17L of coupling means 12L to an opening facing microphone 18L.

The speakers 15R, 15L and the microphones 18R, 18L form part of a noise detection and cancellation control unit 19 which includes a microprocessor based multi-channel controller unit 20. A commercially available controller 20 that could be used with the present invention is the NCT 2000 controller marketed by Noise Cancellation Technologies, Inc., and therefore further details of that controller are dispensed with herein.

The noise attenuation system of FIG. 3 operates as follows. The undesirable noise that is generated in the area of the patients head during magnetic resonance scanning operations is communicated via the respective openings 17R, 17L and hollow tubes 16R, 16L to the respective microphones 18R and 18L. The signals from these microphones 18R and 18L are supplied to different channels of the controller 20, where they are processed, and a cancelling sound wave pattern is supplied by the controller 20 to drive the speakers 15R and 15L as a function of the sound wave pattern reaching the microphones. The antinoise sound waves are transmitted from the respective speakers 15R, 15L via the hollow tubes 13R, 13L to the openings 14R, 14L of the respective ear coupling means, to thereby apply a cancelling noise wave pattern into the ear coupling means to substantially attenuate the noise the patient P is subjected to.

In preferred practical embodiments of the invention, the tubes 13R, 13L, 16R, 16L are constructed as hollow vinyl tubes with an outside diameter of, for example, ½-inch and an inside diameter of, for example, ⅜-inch. The diameter of the tubes are sufficiently smaller than the length of the tube to negate any destructive interference, the wave velocity impedance for any given diameter and length being the main consideration in selecting these dimensions. Such hollow tubes are sufficiently flexible to accommodate positioning thereof with respect to the headset and the MRI equipment so as to minimize disruption of the conventionally available MRI equipment. Since the hollow tubes 13R, 13L, 16R, 16L are made of non-magnetic, non-metallic materials and since they protrude from the outside into the chamber 6, the sound attenuation system 10 does not interfere with the magnetic resonance scanning operation. The headset ear coupling means 12R, 12L are likewise preferably constructed of non-magnetic, non-metallic material, such as plastic, so as not to interfere with the magnetic fields being generated.

According to the invention, the openings 14R and 17R of the ear coupling means 12R are located sufficiently close to one another so that the detected unwanted sound wave pattern transmitted via opening 17R and tube 16R and sensed by microphone 18R is an accurate real time representation of the sound that should be generated by the speaker 15R and transmitted via tube 13R and opening 14R to the ear coupling means 12R, thereby resulting in an optimum noise cancellation sound wave as experienced by the patient P. The left side ear coupling means and tubes, speakers and microphones likewise are configured for optimum noise cancellation.

According to certain preferred embodiments, the tubes 13R, 13L can also be used to transmit pleasant sounds to the patient P such as music or the like, which music pattern will not disrupt the noise cancellation waves. In such embodiments, not only is the undesirable noise level substantially reduced, the pleasant music sound can be provided with optimum fidelity.

Figure 4:
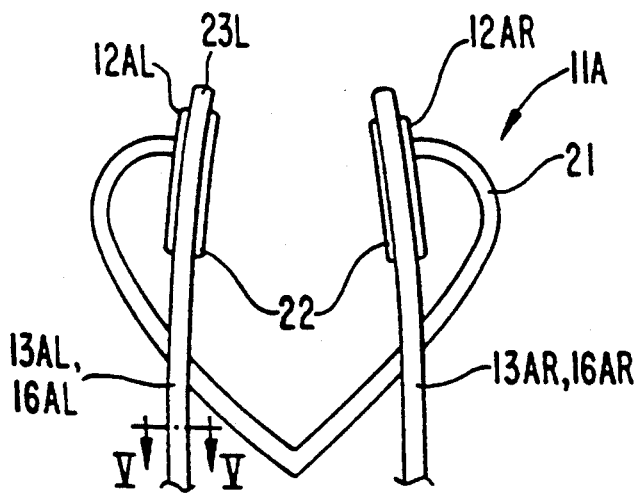
FIG. 4 is an enlarged schematic view of a preferred embodiment of a headset having an open ear coupling means arrangement for the sound attenuation system of FIGS. 1 and 3.
Figure 5:
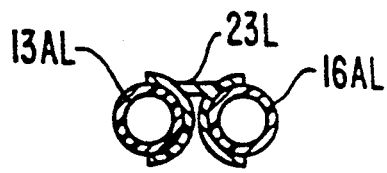
FIG. 5 is an enlarged sectional view taken along line V—V of FIG. 4.

FIG. 4 schematically depicts a preferred form of construction of the headset having an open ear coupling means. Referring to FIG. 4, the headset 11A includes a right ear coupling means 12AR and a left ear coupling means 12AL. The ear coupling means 12AR and 12AL are held together by a resilient yoke 21 and each include a foam padding 22 at the side facing the patients ears. As shown in FIG. 5, the hollow tubes 13AL and 16AL of the left ear coupling means 12AL may be joined together to facilitate handling, for example, in a rigid plastic mounting 23L which merges into the ear coupling means 12AL. The resilient yoke 21 is coupled to the headset via rigid plastic mounting 23L. The hollow tubes 13AL and 16AL open near the ear at predetermined spaced locations along the rigid plastic mounting 23L. Since the efficiency of the perceived noise cancellation is determined by the quality of the coupling of the counternoise to the ear, in an open system as depicted by FIG. 4, close proximity of the ear coupling means to the patient's ear is preferred. The tubes for the right ear coupling means 12AR are constructed similarly.

Although the preferred illustrated embodiments include headsets with ear coupling means that cup over the patients ears, embodiments are also contemplated wherein the magnetic resonance unit is outfitted with permanently fixed supports for the hollow tubes for detecting the unwanted sound to be cancelled and for transmitting the counternoise cancelling sound waves. These tubes can be held in a predetermined position adjacent the table 2, with adjustment provisions being provided to position the same for differently shaped heads.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A patient diagnosing apparatus comprising:
   patient accommodating means for holding a patient in a predetermined position in an ambient environment:
   diagnosing means operatively coupled to and surrounding said patient accommodating means, for diagnosing a medical condition of the patient, said diagnosing means generating undesirable acoustic noise in an area of the patient during a diagnosis operation: and
   active noise cancellation means, adapted to be coupled to the patient for canceling the undesirable acoustic noise generated by said diagnosing means in said area of the patient, said active noise cancellation means comprising:
   first non-magnetic, nonmetallic flexible sound propagating means for carrying said undesirable acoustic noise, and
   noise detection means, for detecting the undesirable acoustic noise in the area of the patient and located remotely from said patient accommodating means and adapted to be coupled to the patient through said first non-magnetic, non-metallic flexible sound propagating means so that detection of the undesirable acoustic noise does not interfere with operation of said diagnosing means, and
   second non-magnetic, non-metallic flexible sound propagating means, for carrying counternoise waves, and
   counternoise speaker means, for generating and transmitting said counternoise waves to the patient based upon the detected undesirable acoustic noise, to cancel the undesirable acoustic noise in the area of the patient, said counternoise speaker means adapted to be located remotely from said patient accommodating means and adapted to be coupled to the patient through said second non-magnetic, non-metallic flexible sound propagating means so that transmission of said counternoise waves does not interfere with operation of said diagnosing means.

2. The patient diagnosing apparatus according to claim 1, wherein said first and second sound propagating means are hollow tubes filled with a sound wave propagating medium.

3. The patient diagnosing apparatus according to claim 1 further comprising:
   a headset including a pair of ear coupling means for coupling said counternoise waves to the auditory system of the patient, said noise detection means and said counternoise speaker means being coupled to said ear coupling means through said first and second sound propagating means respectively; and
   control means coupled to said noise detection means and said counternoise speaker means for controlling generation of said counternoise waves of respective channels for each respective one of said ear coupling means as a function of said detected undesirable acoustic noise detected at each respective one of said ear coupling means.

4. The patient diagnosing apparatus according to claim 3, wherein said first and second sound propagating means are hollow tubes filled with a sound wave propagating medium.

5. The patient diagnosing apparatus according to claim 3, wherein each of said ear coupling means comprises cup-shaped means adapted to be fitted on the patient so that the patient's ears are isolated from said ambient environment.

6. The patient diagnosing apparatus according to claim 3, wherein each of said ear coupling means comprise respective open-ear coupling means for fitting on the patient.

7. A patient diagnosing apparatus comprising:
   patient accommodating means for holding a patient in a predetermined position;
   diagnosing means, operatively coupled to and surrounding said patient accommodating means, for diagnosing a medical condition of the patient, said diagnosing means generating undesirable acoustic noise in an area of the patient during a diagnosis operation; and
   active acoustic noise cancellation means, coupled to said diagnosing means, for canceling the undesirable acoustic noise generated by said diagnosing means in the area of the patient, said active acoustic noise cancellation means comprising.
   first non-magnetic, non-metallic flexible sound propagating means adapted to carry undesirable acoustic noise, and
   noise detection means, for detecting the undesirable acoustic noise in the area of the patient, located remotely from said patient accommodating means and coupled to said diagnosing means through said first non-magnetic, non-metallic flexible sound propagating means so that detection of the undesirable acoustic noise does not interfere with the operation of said diagnosing means, and
   second non-magnetic, non-metallic flexible sound propagating means, adapted to carry counternoise waves, and
   counternoise speaker means, for generating and transmitting said counternoise waves to the patient based upon the detected undesirable acoustic noise, to cancel the undesirable acoustic noise in the area of the patient, said counternoise speaker means located remotely from said patient accommodating means and coupled to said diagnosing means through said second non-magnetic, non-metallic flexible sound propagating means so that transmission of the counternoise waves does not interfere with operation of said diagnosing means.

8. The patient diagnosing apparatus according to claim 7, wherein said first and second sound propagating means are elongated hollow tubes filled with a sound wave propagating medium.

9. The patient diagnosing apparatus according to claim 8, wherein said sound wave propagating medium is air.

10. The patient diagnosing apparatus according to claim 7, wherein said diagnosing means includes magnetic resonance scanning means for scanning patient for diagnostic purposes.

11. The patient diagnosing apparatus of claim 7, said active noise cancellation means further comprising:
control means, coupled to said noise detection means and said counternoise speaker means, for controlling generation of said counternoise waves of respective channels for each respective ear of the patient as a function of said detected undesirable acoustic noise detected at each respective ear.

12. A method of canceling undesirable acoustic noise generated by diagnosing means in the area of a patient's ear during a patient diagnosis operation, comprising the steps of:
transferring the undesirable noise generated by the diagnosing means from the area of the patient's ear to a remote location via first elongated, flexible non-magnetic sound propagating means;
detecting the transferred undesirable acoustic noise using noise detection means at the remote location so that said detecting does not interfere with the patient diagnosis operation;
generating counternoise waves using control means at the remote location based upon the detected undesirable acoustic noise so that said generating does not interfere with the patient diagnosis operation; and transferring the counternoise waves generated by the control means from the remote location to the area of the patient's ear via second elongated, flexible non-magnetic, non-metallic sound propagating means to cancel the undesirable acoustic noise in the immediate area of the patient's ear.

13. The method of cancelling undesirable acoustic noise of claim 12, wherein said steps of transferring comprises the steps of transferring the undesirable acoustic noise and the counternoise waves via hollow tubes filled with a sound propagating medium.

14. The method of cancelling undesirable acoustic noise of claim 13, wherein said steps of transferring comprises the steps of transferring the undesirable acoustic noise and the counternoise waves via hollow tubes filled with air.

15. The method of cancelling undesirable acoustic noise of claim 13, wherein said steps of transferring comprises the steps of transferring the undesirable acoustic noise and the counternoise waves via hollow tubes filled with liquid.

16. The method of cancelling undesirable acoustic noise of claim 13, said steps of transferring comprising:
transferring the undesirable acoustic noise from the area of the patient to the remote location and the counternoise waves from the remote location to the area of the patient via a headset including cup-like ear coupling means so that the ears of the patient are isolated from the undesirable acoustic noise.

17. The method of cancelling undesirable acoustic noise of claim 13, said steps of transferring comprising:
transferring the undesirable acoustic noise from the area of the patient to the remote location and the counternoise wave from the remote location to the area of the patient via said first and second sound propagating means which are operatively coupled to the diagnosing means.

18. A noise cancellation system for a patient diagnosis apparatus comprising:
active noise cancellation means, located remotely from the patient diagnosis apparatus, for cancelling undesirable acoustic noise generated by the patient diagnosis apparatus in an area of a patient during a diagnosis operation, said active noise cancellation means comprising
first and second microphones for detecting the undesirable acoustic noise in respective first and second areas immediately near the ears of the patient,
control means, coupled to said first and second microphones, for generating respective first and second cancellation waves based upon the undesirable acoustic noise of said first and second areas, and
first and second speakers, coupled to said control means, for respectively transmitting said first and second cancellation waves to said first and second areas to cancel the undesirable acoustic noise, and
non-magnetic, non-metallic sound propagating means, coupled to said active noise cancellation means, said propagating means adopted to transfer the undesirable acoustic noise from said first and second areas to said first and second microphones and for transferring said first and second cancellation waves from said first and second speakers to said first and second areas.

19. The noise cancellation system of claim 18, wherein said sound propagating means comprises hollow tubes filled with a sound propagating medium.

20. The noise cancellation system of claim 19, wherein said sound propagating medium is air.

21. The noise cancellation system of claim 19, wherein said sound propagating medium is liquid.

22. The noise cancellation system of claim 18, further comprising a headset with ear coupling means of cup-like configuration for enclosing and isolating each ear of the patient from the ambient environment, said first and second areas respectively located within said ear coupling means.

23. The noise cancellation system of claim 22, wherein said headset with ear coupling means is of an open-backed coupling configuration.

24. The noise cancellation system of claim 18, wherein said sound propagating means is adapted to be mounted on the patient diagnosis apparatus and positioned near each ear of the patient within said first and second areas, respectively.

* * * * *